United States Patent [19]

Richardson

[11] 4,198,435

[45] Apr. 15, 1980

[54] PHARMACEUTICAL COMPOSITIONS

[75] Inventor: Dora N. Richardson, Macclesfield, England

[73] Assignee: Imperial Chemical Industries Limited, London, England

[21] Appl. No.: 874,481

[22] Filed: Feb. 2, 1978

[51] Int. Cl.² .......................................... A61K 31/135
[52] U.S. Cl. .................................................... 424/330
[58] Field of Search ........................................ 424/330

[56] References Cited

PUBLICATIONS

Fromson et al., Xenobiotica, 1973, vol. 3, No. 11, pp. 693–703.

*Primary Examiner*—Jerome D. Goldberg
*Attorney, Agent, or Firm*—Cushman, Darby & Cushman

[57] ABSTRACT

The use of 1-(p-β-dimethylaminoethoxyphenyl)-trans-1-(p-hydroxyphenyl)-2-phenylbut-1-ene as an anti-oestrogenic agent and pharmaceutical compositions containing this compound.

5 Claims, No Drawings

PHARMACEUTICAL COMPOSITIONS

This invention relates to pharmaceutical compositions containing a triphenylbut-1-ene derivative and the use of the compound or compositions as an anti-oestrogen.

It is known from J.Reprod. Fert. (1967), 13, 101 that 1-(p-β-dimethylaminoethoxyphenyl)-trans-1,2-diphenylbut-1-ene (tamoxifen) shows anti-oestrogenic activity in rats and, in this species, is weakly and atypically oestrogenic. It is also known from Xenobiotica (1973), 3, 693, that 1-(p-β-dimethylaminoethoxyphenyl)-trans-1-(p-hydroxyphenyl)-2-phenylbut-1-ene is a major metabolite of tamoxifen in the dog, but the pharmacological properties of this compound have not been described in the literature.

We have now found that 1-(p-β-dimethylaminoethoxyphenyl)-trans-1-(p-hydroxyphenyl)-2-phenylbut-1-ene (compound I) shows anti-oestrogenic activity of the same order as that shown by tamoxifen, but in contrast to the oestrogenic activity expected in a hydroxy compound of this type, compound I shows only the weak and atypical oestrogenic activity also shown by tamoxifen.

In this specification, the designation "trans" refers to the relative positions of the p-hydroxyphenyl group and the unsubstituted phenyl group about the double bond.

According to the invention there is provided a method of producing an anti-oestrogenic effect in warm blooded animals which require such treatment, which comprises administering orally or parenterally to such a warm blooded animal, an effective amount of compound I or a pharmaceutically acceptable salt thereof.

The anti-oestrogenic activity of compound I has been demonstrated by its effect in preventing implantation of the fertilised ovum when administered by intraperitoneal injection to rats at a dose of 0.02 mg./kg. on each of days 3, 4 and 5 of pregnancy, or when dosed orally at 0.15 mg./kg. on day 4. Anti-oestrogenic activity has also been demonstrated by its effect in inhibiting oestradiol-induced vaginal cornification in ovariectomised rats.

The weak oestrogenic activity of compound I has been demonstrated by its effect in producing cornified vaginal smears in spayed rats at doses of 20–40 mg./kg. on each of three days. Overt toxicity was not observed at these doses.

A compound with the above pharmacological properties is of value in the treatment of the same conditions in which tamoxifen is beneficial, in particular, in the treatment of anovulatory infertility.

When used to produce an anti-oestrogenic effect in warm blooded animals, a typical daily dose is from 0.05 to 1 mg./kg. administered orally, or by injection. In use, tamoxifen has been administered orally at doses of from 20–80 mg./day for the treatment of anovulatory infertility. A similar regime is appropriate for the administration of compound I, most conveniently in the form of a pharmaceutical composition.

According to a further feature of the invention, there is provided a pharmaceutical composition comprising compound I or a pharmaceutically acceptable salt thereof together with a pharmaceutically acceptable diluent or carrier.

A particularly suitable salt is, for example, a hydrochloride, sulphate, phosphate, acetate, tartrate or citrate.

The composition may be in a form suitable for oral or parenteral administration. A tablet or capsule is a particularly convenient form for oral administration, and such a composition may be made by conventional methods and contain conventional excipients. Thus a tablet could contain diluents, for example a mannitol or maize starch, disintegrating agents, for example alginic acid, binding agents, for example methylcellulose, and lubricating agents, for example magnesium stearate.

A composition for oral administration may conveniently contain from 5–50 mg. of compound I, preferably 5–20 mg.

Compound I may be obtained as follows:

A solution of p-(2-tetrahydropyranyloxy)phenyl magnesium bromide was prepared in the usual manner from 1.65 g. of magnesium and 8.48 g. of p-(2-tetrahydropyranyloxy) bromobenzene in a mixture of 30 ml. of dry ether and 30 ml. of dry tetrahydrofuran. To this solution was added a solution of 9.33 g. of 4-(β-dimethylaminoethoxy)-α-ethyldesoxybenzoin in 50 ml. of ether. The mixture was heated under reflux for 2 hours, cooled and decomposed by the addition of saturated ammonium chloride solution. The organic layer was separated, and the aqueous layer was extracted with ether. The combined organic layers were dried and evaporated to give 1-(p-β-dimethylaminoethoxyphenyl)-1-[p-(2-tetrahydropyranyloxy)phenyl]-2-phenylbutan-1-ol as an oil. This compound was dissolved in 100 ml. of ethanol, and the solution acidified with concentrated hydrochloric acid. It was then heated under reflux for 2 hours, cooled and the solvent evaporated. The residual gum was stirred with water, and made alkaline by the addition of ammonia solution. The precipitated material was extracted with ether, the ethereal extract dried, and evaporated to give a mixture of the isomers of 1-(p-β-dimethylaminoethoxyphenyl)-1-(p-hydroxyphenyl)-2-phenylbut-1-ene. 10.0 g. of this mixture was then stirred with 100 ml. of chloroform, and the insoluble material was crystallised several times from acetone to give 1-(p-β-dimethylaminoethoxyphenyl)-trans-1-(p-hydroxyphenyl)-2-phenylbut-1-ene, m.p. 142°–144° C.

The invention is illustrated but not limited by the following Example.

EXAMPLE

Tablets were made by granulating a mixture of 1-(p-β-dimethylaminoethoxyphenyl)-trans-1-(p-hydroxyphenyl)-2-phenylbut-1-ene (compound I) or its citrate with mannitol and maize starch in the presence of alginic acid and then mixing the dried granules with methylcellulose and magnesium stearate followed by compression into tablets. A typical tablet had the composition:

Compound I—10 mg.
Mannitol—111 mg.
Maize starch—15 mg.
Alginic acid—6 mg.
Methyl cellulose—0.75 mg.
Magnesium stearate—1.5 mg.

What we claim is:

1. A pharmaceutical composition in the form of a tablet or capsule for obtaining an antioestrogenic effect comprising an anti-oestrogenically effective amount of 1-(p-β-dimethylaminoethoxyphenyl)-trans-1-(p-hydroxyphenyl)-2-phenylbut-1-ene or a pharmaceutically acceptable salt thereof together with a pharmaceutically acceptable diluent or carrier.

2. A composition as claimed in claim 1 wherein the pharmaceutically acceptable salt is a hydrochloride, sulphate, phosphate, acetate, tartrate or citrate.

3. A composition as claimed in claim 1 which contains from 5–50 mg. of 1-(p-β-dimethylaminoethoxyphenyl)-trans-1-(p-hydroxyphenyl)-2-phenylbut-1-ene or the equivalent amount of a pharmaceutically acceptable salt thereof.

4. A method of producing an anti-oestrogenic effect in warm blooded animals which require said treatment, which comprises administering orally or parenterally to said warm blooded animal, an anti-oestrogenically effective amount of 1-(p-β-dimethylaminoethoxyphenyl)-trans-1-(p-hydroxyphenyl)-2-phenylbut-1-ene or a pharmaceutically acceptable salt thereof.

5. A method as claimed in claim 4 wherein the 1-(p-β-dimethylaminoethoxyphenyl)-trans-1-(p-hydroxyphenyl)-2-phenylbut-1-ene is administered in a dose of from 0.05 to 1 mg./kg.

* * * * *

UNITED STATES PATENT AND TRADEMARK OFFICE
CERTIFICATE OF CORRECTION

PATENT NO. : 4,198,435
DATED : April 15, 1980
INVENTOR(S) : Dora N. Richardson

It is certified that error appears in the above-identified patent and that said Letters Patent are hereby corrected as shown below:

On the face of the patent add Item [30]

--[30] Foreign Application Priority Data

February 28, 1977    United Kingdom    8273/77 --.

*Signed and Sealed this*

*Fifth* Day of *August 1980*

[SEAL]

Attest:

SIDNEY A. DIAMOND

Attesting Officer    *Commissioner of Patents and Trademarks*